United States Patent [19]

Bazin et al.

[11] Patent Number: 4,976,272

[45] Date of Patent: Dec. 11, 1990

[54] METHOD AND DEVICE FOR MEASURING THE ELASTICITY OF A SUPERFICIAL LAYER, IN PARTICULAR OF THE SKIN

[75] Inventors: Roland M. Bazin, Vitry S/Seine; Gérard Obadia, Montrouge; Louis Marcotte, Chevilly La Rue - Rungis; Jean Scot, Paris, all of France

[73] Assignee: L'Oreal, Paris, France

[21] Appl. No.: 331,398

[22] Filed: Mar. 31, 1989

[30] Foreign Application Priority Data

Mar. 31, 1988 [FR] France .................................. 88 04292

[51] Int. Cl.$^5$ ............................................... A61B 5/10
[52] U.S. Cl. .......................................... 128/774; 73/37
[58] Field of Search .................... 128/774; 73/37, 37.5, 73/104, 714

[56] References Cited

FOREIGN PATENT DOCUMENTS

| | | | |
|---|---|---|---|
| 3445587 | 6/1986 | Fed. Rep. of Germany | 128/774 |
| 733686 | 10/1932 | France | 128/774 |
| 2068567 | 8/1981 | United Kingdom. | |

OTHER PUBLICATIONS

Engineering in Medicine, vol. 8, No. 2 Apr. 1979, pp. 105, 106, "Continuous tissue pressure monitor".

Primary Examiner—Randall L. Green
Assistant Examiner—Randy Shay
Attorney, Agent, or Firm—Cushman, Darby & Cushman

[57] ABSTRACT

The method for measuring the elasticity of a superficial layer (2), in particular of the skin, comprises defining a zone (7) of this layer; creating a negative pressure in this zone to cause a deformation of the zone; and measuring the negative pressure necessary to cause a deformation of predetermined amplitude. The measuring device includes a sensor (3) provided with a cavity (5) defined by a rim (6) arranged to be pressed against the layer (2) to be studied, and a pump (17) for creating a negative pressure in the cavity (5). A suction opening (20) is provided in the cavity at a predetermined distance (d) from the superficial layer, in such a manner as to be obturated by the layer when the deformation attains the predetermined amplitude. A pick-up device is provided for measuring the negative pressure that has produced the deformation of predetermined amplitude.

8 Claims, 1 Drawing Sheet

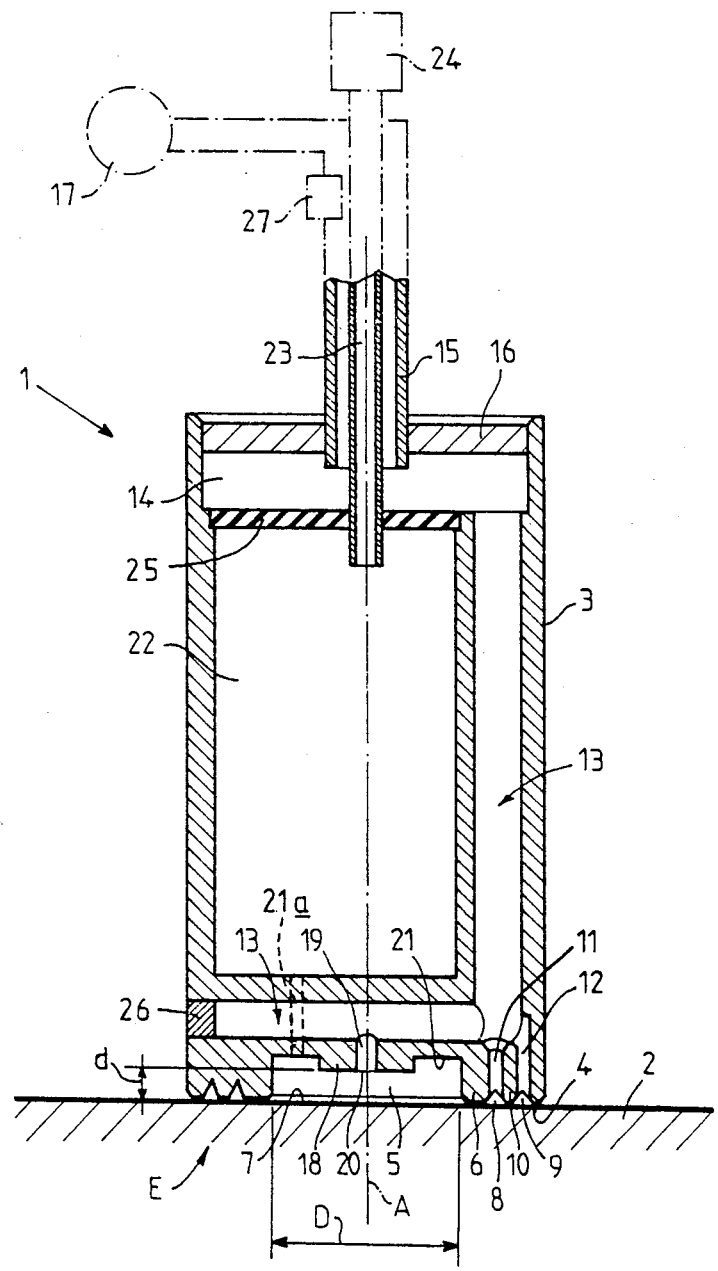

METHOD AND DEVICE FOR MEASURING THE ELASTICITY OF A SUPERFICIAL LAYER, IN PARTICULAR OF THE SKIN

FIELD OF THE INVENTION

The invention relates to a method for measuring the elasticity of a superficial layer, in particular of the skin, of the kind by by which a zone of this layer is defined, and negative pressure is created on the zone to cause deformation of the zone.

BACKGROUND OF THE INVENTION

The methods proposed thus far, while giving satisfaction, are relatively complicated to use and do not make it possible to attain a quasi-automatic and instantaneous measurement of the elasticity.

SUMMARY OF THE INVENTION

The primary object of the invention is to embody the method, of the type defined above, such that it is more responsive than before to various practical requirements, and in particular such that it permits rapid and practically automatic measurement and is simple to use.

According to the invention, the method for measuring the elasticity of a surface layer, in particular of the skin, of the above-defined type, is characterized in that the negative pressure necessary to create a deformation of predetermined amplitude in the layer is measured.

Advantageously, the deformation of predetermined amplitude is detected by obturating a suction opening located at an initial predetermined distance from the superficial layer. This predetermined distance may be selected equal to 2.5 mm. The invention also relates to a device for measuring the elasticity of a superficial layer, in particular of the skin, for performing the above-defined method. Such a device includes a sensor provided with a cavity, defined by a rim arranged to be pressed against the layer to be studied to define the zone, means for creating a negative pressure in the cavity and causing the deformation of the zone, an opening provided in the cavity, at a predetermined initial distance from the superficial layer, and disposed in such a manner as to be obturated by the layer when the deformation attains a predetermined amplitude, and means for measuring the negative pressure which has produced this deformation of predetermined amplitude; according to the invention, this device is characterized in that it includes means sensitive to the deformation of the superficial layer when the deformation attains an amplitude of predetermined value, and means for measuring the negative pressure that have produced this deformation of predetermined amplitude.

Preferably, the aforementioned sensitive means include a suction opening, provided in said cavity, at a predetermined initial distance from the superficial layer, this opening being disposed in such a manner as to be obturated by the layer when the deformation attains the predetermined amplitude.

Advantageously, the cavity includes in its bottom a projection portion penetrated by a passage for communication with an internal conduit system connected to a source of negative pressure the end of the passage discharging into the cavity comprising the opening is intended to be obturated by the deformed zone of the superficial layer.

Advantageously, the sensor has an end face intended to be pressed against the superficial layer, this end face being located in a plane situated at a distance on the order of 2.5 mm from the plane of the opening. The diameter of the cavity may be on the order of 15 mm.

The central zone of the face which which the sensor rests on the superficial layer is occupied by this cavity, and this support or resting face includes means, surrounding the cavity, that are arranged for sealing between the sensor and the superficial layer.

These scaling means may include at least one peripheral groove, in particular with a cross section in the form of an inverted V surrounding the cavity, and connected to the source of negative pressure. Preferably, two concentric peripheral throats are provided.

A valve may be provided, arranged to open when the suction opening provided in the cavity is closed by the deformed superficial layer.

In an advantageous embodiment, the sensor includes a closed chamber having a volume greater than that of the cavity, this chamber being connected to the cavity by a conduit, and the entire assembly being such that when the suction opening of the cavity is closed, the pressure in the chamber remains practically constant. Preferably, the device includes a tube discharging into the chamber and connected to a pressure pickup, to enable measuring the pressure in the chamber and the cavity when the cavity is closed by the deformed superficial layer.

The sensor may have the shape of a cylinder of revolution, the lower transverse face of which is intended to be pressed against the superficial layer; the central portion of this lower face includes the aforementioned cavity surrounded by a circular rim provided with two peripheral grooves connected to the source of negative pressure. The chamber is provided in an intermediate zone along the length of the cylinder and is connected to the cavity via a conduit in a region located outside the portion projecting from the bottom of the cavity. This chamber is also connected, on the side opposite the cavity, to a tube that is coaxial with a primary tube of larger diameter, connected to the source of negative pressure and communicating on the inside of the cylinder with an internal conduit system connected respectively to the peripheral grooves and to the opening discharging into the cavity.

Besides the features described above, the invention also includes a number of other features that will be described in further detail below in terms of an exemplary but in no way limiting embodiment, in conjunction with the drawing.

BRIEF DESCRIPTION OF THE DRAWING

The single drawing FIG. 1 is a schematic longitudinal section through a device in accordance with the invention for measuring the elasticity of a superficial layer, in particular of the human skin.

DESCRIPTION OF THE PREFERRED EMBODIMENT

Turning to the drawing, a device 1 can be seen for measuring the elasticity of a superficial layer, which in the exemplary embodiment in questions comprises the skin 2. The device 1 includes a sensor 3, advantageously of cylindrical form, which includes a face 4 with which it contacts or rests on the skin 2.

The face 4 is located in a plane orthogonal with the axis A of the sensor. The central region of the face 4 is occupied by a cavity 5, which is advantageously circular and is defined by a rim 6 arranged to be pressed against the skin to define a zone 7 that will be subjected to deformation.

The rest face 4 includes means E surrounding the cavity 5 and the rim 6 which are arranged to effect tightness between the sensor 3 and the skin 2. Advantageously, these sealing means E include two concentric grooves 8, 9 centered on the axis A and separated from one another by a rib 10 arranged to be pressed against the skin 2. The cross section of the grooves 8, 9 is in the form of an inverted V. Each groove 8, 9 is connected by a respective conduit 11, 12 to an internal conduit system 13 of the sensor, which communicates with a housing 14 provided toward the end of the sensor remote from the face 4. A tube 15 that is coaxial with the sensor 3 penetrates the upper transverse wall 16 of the sensor and discharges in the housing 14. This tube 15, which is preferably flexible, is connected at its other end to a small air pump 17 of constant output.

In its bottom, the cavity 5 includes a projecting portion 18 penetrated by a passage 19 for connection with the internal conduit system 13, which in turn is connected to the source of negative pressure comprising the pump 17. The diameter D of the cavity 5 may be on the order of 15 mm.

The end of the passage 19 discharging into the cavity 5 comprises an opening 20 intended to be obturated by the zone 7 of the skin when it is deformed under the influence of negative pressure. The distance d between the plane of the end face 4 of the sensor (and hence the zone 7 prior to deformation) and the face of the projection 18 is advantageously equal to 2.5 mm, or in the vicinity of this figure. The remaining portion 21 of the bottom of the cavity 5 is indented with respect to the projection 18 and forms an annular groove. A conduit 21a substantially parallel to axis A is provided in the sensor and discharges at one end in the portion 21 and at its other end into a closed chamber 22, the volume of which is notably greater than that of the cavity 5. A tube 23 of reduced diameter by comparison with the tube 15 discharges into the chamber 22 and is disposed substantially coaxially with the tube 15. The tube 23 is connected to a relative pressure pickup 24 making it possible to determine the pressure in the chamber 22 and hence in the cavity 5. The pickup is located in a control box. The tube 23 penetrates the wall defining the chamber 22 in a sealed manner.

The chamber 22 is closed in its upper portion by an attached lid 25 that is fixed in a sealed manner.

The provision of the various passages, channels and systems of internal conduits in the sensor 3 may necessitate the drilling of bores discharging to the outside. The openings of these bores at the outside surface of the sensor are then obturated with plugs such as 26, made of some suitable material.

A valve 27, schematically shown here, may be provided on the tube 15 connected to the pump and may be calibrated such that it opens when the suction opening 20 is closed by the deformed skin 2.

In any case, to effect a measurement of the elasticity of the skin with the device according to the invention, the method used is as follows.

A zone 7 of the skin to which the measurement is to pertain is defined, by placing the sensor 1 with its axis A substantially perpendicular to the region in question of the skin 2; the rim 6 of the cavity 5 then defines this zone 7. Next, the pump 17 is turned on, which creates a negative pressure, in particular in the grooves 8 and 9, by the suction of air through the passages 11 and 12 and through the internal conduit system 13 of the sensor and through the tube 15.

The pump 17 is selected such that its output is sufficient to create a negative pressure in the grooves 8 and 9, which press the sensor 1 against the skin 2 in a sealed manner. The initial negative pressure necessary to obtain clinging and tightness at the level of the grooves 8 and 9 is on the order of 100 millibars.

The grooves 8 and 9, maintained at negative pressure by the passages 12 and 11, assure that the sensor will be held tightly against the skin.

The pump 17 has a capacity sufficient to effect the clinging of the sensor during the entire measurement. This pump 17 may comprise a mini-pump with high-speed vanes (the speed may be higher than 500 rpm).

Once the clinging phase has been effected, the skin is deformed at the level of the grooves 8 and 9 and has to come to obturate the end of the conduits 11 and 12.

The measurement phase then commences; the suction occurs substantially in the cavity 5 through the passage 19.

The zone 7 of the skin 2 is rapidly sucked up; as it deforms, it comes to obturate the opening 20. At that moment, the pressure in the chamber 22, which is of large capacity and is connected to the cavity 5, undergoes no further change in the direction of a reduction.

The value of this pressure measured through the tube 23, via the pickup 24, corresponds to the negative pressure necessary to deform the zone 7 of skin by a predetermined distance corresponding to the distance d, the value of which is 2.5 mm in the example in question.

This distance d and the diameter D of the cavity 5 are advantageously selected such that the negative pressure necessary for obturating the opening 20 will be between 20 and 85 millibars.

Thus, according to the invention, the negative pressure necessary to create a constant deformation, for instance of 2.5 mm, is measured.

The measurement sensor 3 is completely pneumatic and permits practically instantaneous measurement.

A small pump 17 of constant output is sufficient.

With the same pump 17, the sensor 3 makes it possible to perform two functions automatically, that is, sealing at the level of the skin with the grooves 8 and 9 and measurement with the aid of the cavity 5.

What is claimed is:

1. In a method of measuring the elasticity of a superficial layer, in particular of the skin, with the use of a sensor apparatus of the type having a face member for engaging the layer, said face member including an opening to a cavity with the opening lying in a plane, the cavity having a projection surface spaced a first distance from the plane and a recess spaced a second distance from the plane with the first distance being less than the second distance, the projection surface including passage means for connection to a source of negative pressure and the recess having passage means for connection to pressure indicating means, the steps comprising (a) applying the opening of the sensor apparatus to a zone of the superficial layer;

(b) applying a negative pressure to the cavity through the passage means of the projection surface to cause a deformation of the zone of the layer sufficient to move the layer in the zone through the first distance to close the passage means of the projection surface; and (c) measuring the amplitude of the negative pressure causing the deformation by the pressure indicating means through the passage means of the recess.

2. A sensor device for measuring the elasticity of a superficial layer, in particular, of the skin, comprising a housing including a cavity surrounded by rim means defining an opening to said cavity with said opening and said rim means lying in a plane, said rim being disposable on the layer to define a zone, said cavity having a projection surface spaced a first distance from said plane, an annular groove in said cavity and spaced a second distance from said plane with said first distance being less than said second distance, said projection surface having passage means connected to a source of negative pressure, said groove having passage means connected to pressure indicating means so that, with said rim means disposed on the layer and sufficient negative pressure applied to said passage means of said projection surface, the layer in the zone will be deformed to move through said first distance to close said passage means of said projection surface and the negative pressure in said groove which causes the deformation will be measured by said pressure indicating means.

3. A device as defined by claim 2, characterized in that the sensor device includes a closed chamber having a volume greater than that of the cavity, said chamber being connected via a conduit to said cavity.

4. The device as claimed in claim 3 wherein said pressure indicating means is connected to said closed chamber by a tube and said passage means of said groove is in communication with said closed chamber.

5. The device as claimed in claim 3 wherein said housing has the shape of a cylinder of revolution having said rim means at one end thereof, said rim means being circular and including two concentric peripheral grooves connected to said source of negative pressure, said closed chamber being located intermediate said cylinder and being connected to said cavity by a conduit which is connected to said passage means of said groove in said cavity, said closed chamber being connected to another tube which extends coaxially within a further tube connected to said source of negative pressure with said further tube being of greater diameter than said another tube, said cylinder having an internal passage connecting said cavity and said peripheral grooves with said source of negative pressure.

6. The device as claimed in claim 2 wherein said cavity includes a bottom wall and said projection surface extends from said bottom wall, said passage means of said projection surface being connected to a conduit system of said device to said surface of negative pressure.

7. The device as claimed in claims 2 or 6 wherein said rim means has at least one peripheral groove formed therein and opening on said rim means, said peripheral groove being in communication with said source of negative pressure so as to retain said rim means in contact with the layer.

8. The device as claimed in claim 2 wherein said passage means of said projection surface includes tube means and valve means in said tube means operating to close said tube means when said passage means of said projection surface is closed by the layer.

* * * * *